United States Patent
Thommen

(10) Patent No.: US 9,017,375 B2
(45) Date of Patent: Apr. 28, 2015

(54) OCCLUDING DEVICE

(75) Inventor: Daniel Thommen, Steinhausen (CH)

(73) Assignee: Carag AG, Baar (CH)

( * ) Notice: Subject to any disclaimer, the term of this patent is extended or adjusted under 35 U.S.C. 154(b) by 994 days.

(21) Appl. No.: 12/438,116

(22) PCT Filed: Aug. 17, 2007

(86) PCT No.: PCT/CH2007/000403
§ 371 (c)(1),
(2), (4) Date: Mar. 30, 2010

(87) PCT Pub. No.: WO2008/022479
PCT Pub. Date: Feb. 28, 2008

(65) Prior Publication Data
US 2010/0185233 A1    Jul. 22, 2010

(30) Foreign Application Priority Data

Aug. 22, 2006 (EP) .................................... 06405352

(51) Int. Cl.
*A61B 17/08* (2006.01)
*A61B 17/00* (2006.01)
(Continued)

(52) U.S. Cl.
CPC ....... *A61B 17/0057* (2013.01); *A61B 17/12099* (2013.01); *A61B 17/12027* (2013.01);
(Continued)

(58) Field of Classification Search
CPC .................... A61B 17/0057; A61B 17/12022; A61B 17/12027; A61B 17/12031; A61B 17/1204; A61B 17/12109; A61B 17/12113; A61B 17/12122; A61B 17/12131; A61B 17/12136; A61B 2017/00637; A61B 2017/00641; A61B 2017/00632; A61B 2017/00619; A61B 2017/00575; A61B 17/12036; A61B 2017/00597; A61B 2017/00606; A61B 2017/00623

USPC ......... 606/213, 215–217, 157, 151, 191, 192, 606/194, 195
See application file for complete search history.

(56) References Cited

U.S. PATENT DOCUMENTS 3,874,388 A    4/1975  King et al.
4,085,757 A *  4/1978  Pevsner ........................ 606/195
(Continued)

FOREIGN PATENT DOCUMENTS

JP    58-027935     6/1983
WO    97/41779 A1  11/1997
(Continued)

*Primary Examiner* — Gregory Anderson
*Assistant Examiner* — Christopher L Templeton
(74) *Attorney, Agent, or Firm* — McDonnell Boehnen Hulbert & Berghoff LLP

(57) ABSTRACT

An occluding device for closing a body passage comprises an occluding body (1), a first position control element (2) and a second position control element (3). The occluding body (1) is a balloon made of a flexible and fluid tight material without shape memory property. The occluding body (1) comprises a proximal chamber (10) and a distal chamber (11) and a connecting Channel (12) connecting these two chambers (10, 11). The occluding body (1) is compressible into a first longitudinal shape. A proximal end of the occluding body (1) is attached to the first position control element (2) and the distal end of the balloon is attached to the second position control element (3). The first position control element (2) and the second position control element (3) are two matching parts of a fluid tight closure of the balloon. No additional stiffening means for stiffening the balloon in its third radially extended but longitudinally compressed State are arranged within the occluding body (1).

19 Claims, 9 Drawing Sheets

(51) Int. Cl.
 *A61B 17/12* (2006.01)
 *A61B 17/22* (2006.01)

(52) U.S. Cl.
 CPC ..... *A61B17/12022* (2013.01); *A61B 17/12122* (2013.01); *A61B 17/12136* (2013.01); *A61B 2017/00575* (2013.01); *A61B 2017/00606* (2013.01); *A61B 2017/00619* (2013.01); *A61B 2017/00623* (2013.01); *A61B 2017/22062* (2013.01); *A61B 2017/22067* (2013.01); *A61B 2017/00557* (2013.01)

(56) References Cited

U.S. PATENT DOCUMENTS

| | | | | |
|---|---|---|---|---|
| 4,441,495 | A * | 4/1984 | Hicswa | 606/195 |
| 4,471,779 | A * | 9/1984 | Antoshkiw et al. | 606/195 |
| 4,836,204 | A * | 6/1989 | Landymore et al. | 606/215 |
| 5,181,921 | A * | 1/1993 | Makita et al. | 606/195 |
| 5,334,217 | A * | 8/1994 | Das | 606/213 |
| 6,077,281 | A * | 6/2000 | Das | 606/151 |
| 6,251,093 | B1 | 6/2001 | Valley et al. | |
| 6,375,668 | B1 * | 4/2002 | Gifford et al. | 606/200 |
| 6,488,706 | B1 * | 12/2002 | Solymar | 623/3.1 |
| 6,692,494 | B1 | 2/2004 | Cooper et al. | |
| 7,632,291 | B2 * | 12/2009 | Stephens et al. | 606/195 |
| 2003/0070676 | A1 | 4/2003 | Cooper et al. | |
| 2003/0149463 | A1 * | 8/2003 | Solymar et al. | 623/1.1 |
| 2004/0254594 | A1 | 12/2004 | Alfaro | |
| 2004/0254625 | A1 * | 12/2004 | Stephens et al. | 623/1.1 |
| 2005/0273135 | A1 | 12/2005 | Chanduszko et al. | |
| 2005/0288706 | A1 * | 12/2005 | Widomski et al. | 606/213 |
| 2006/0106361 | A1 * | 5/2006 | Muni et al. | 604/500 |
| 2006/0122647 | A1 * | 6/2006 | Callaghan et al. | 606/213 |
| 2007/0250115 | A1 * | 10/2007 | Opolski et al. | 606/215 |
| 2007/0276415 | A1 * | 11/2007 | Kladakis et al. | 606/151 |

FOREIGN PATENT DOCUMENTS

| | | |
|---|---|---|
| WO | 02/38051 | 5/2002 |
| WO | 2005/020786 | 3/2005 |

* cited by examiner

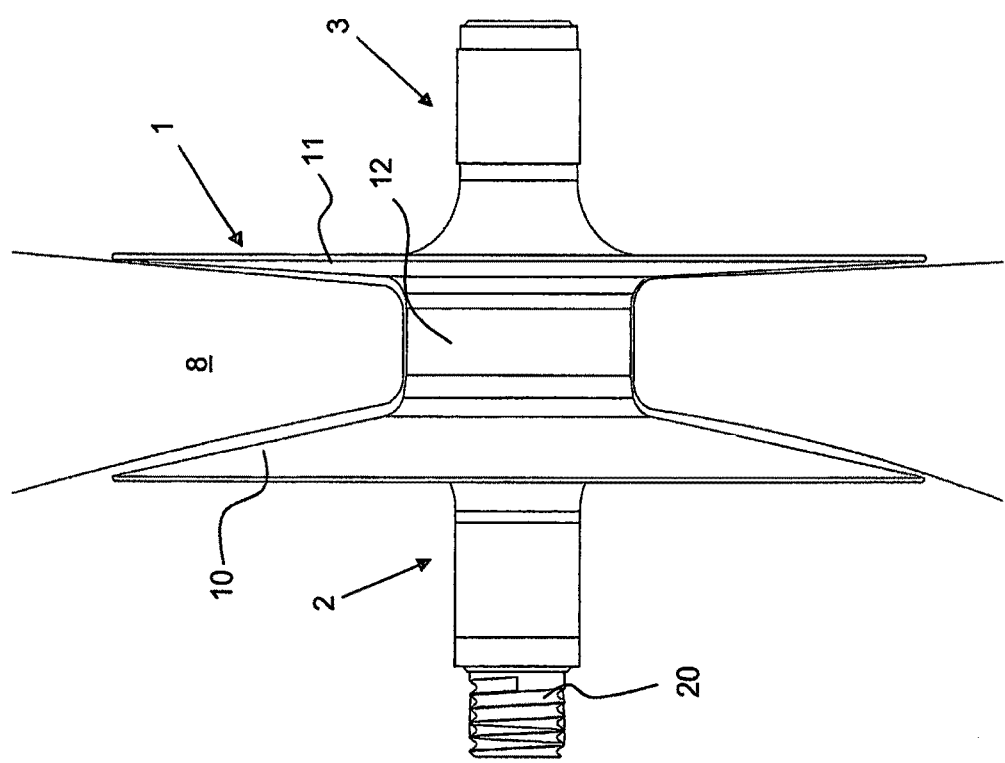

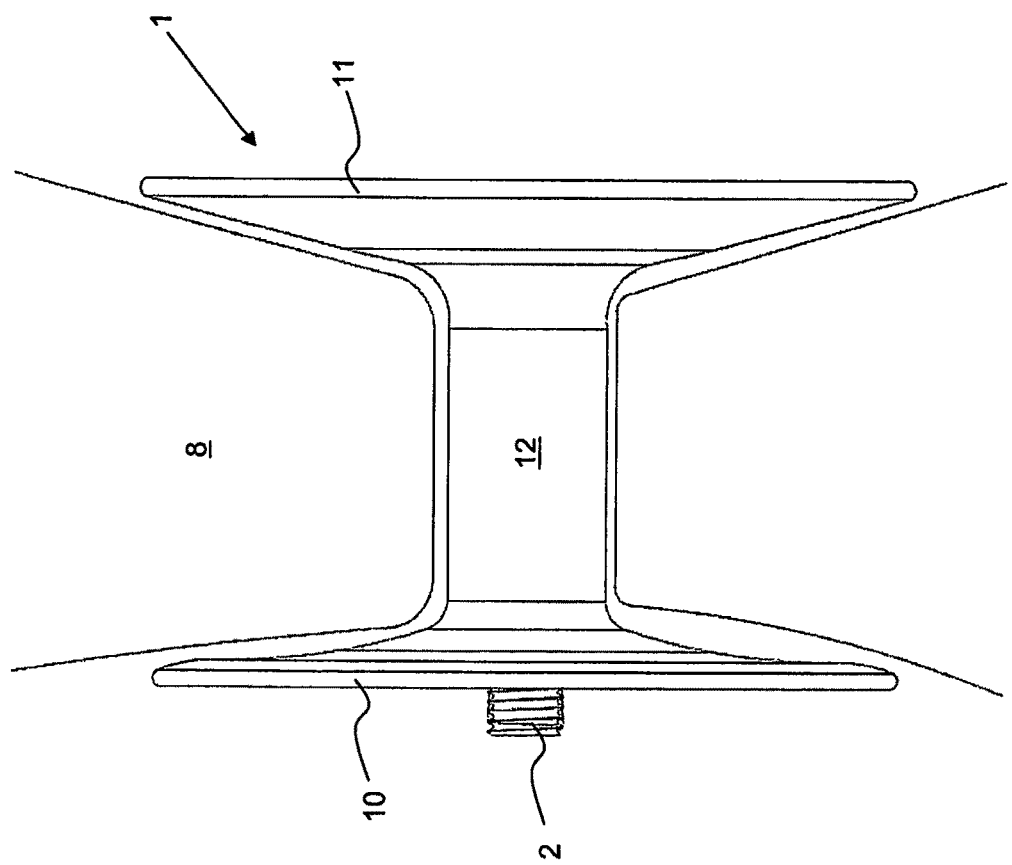

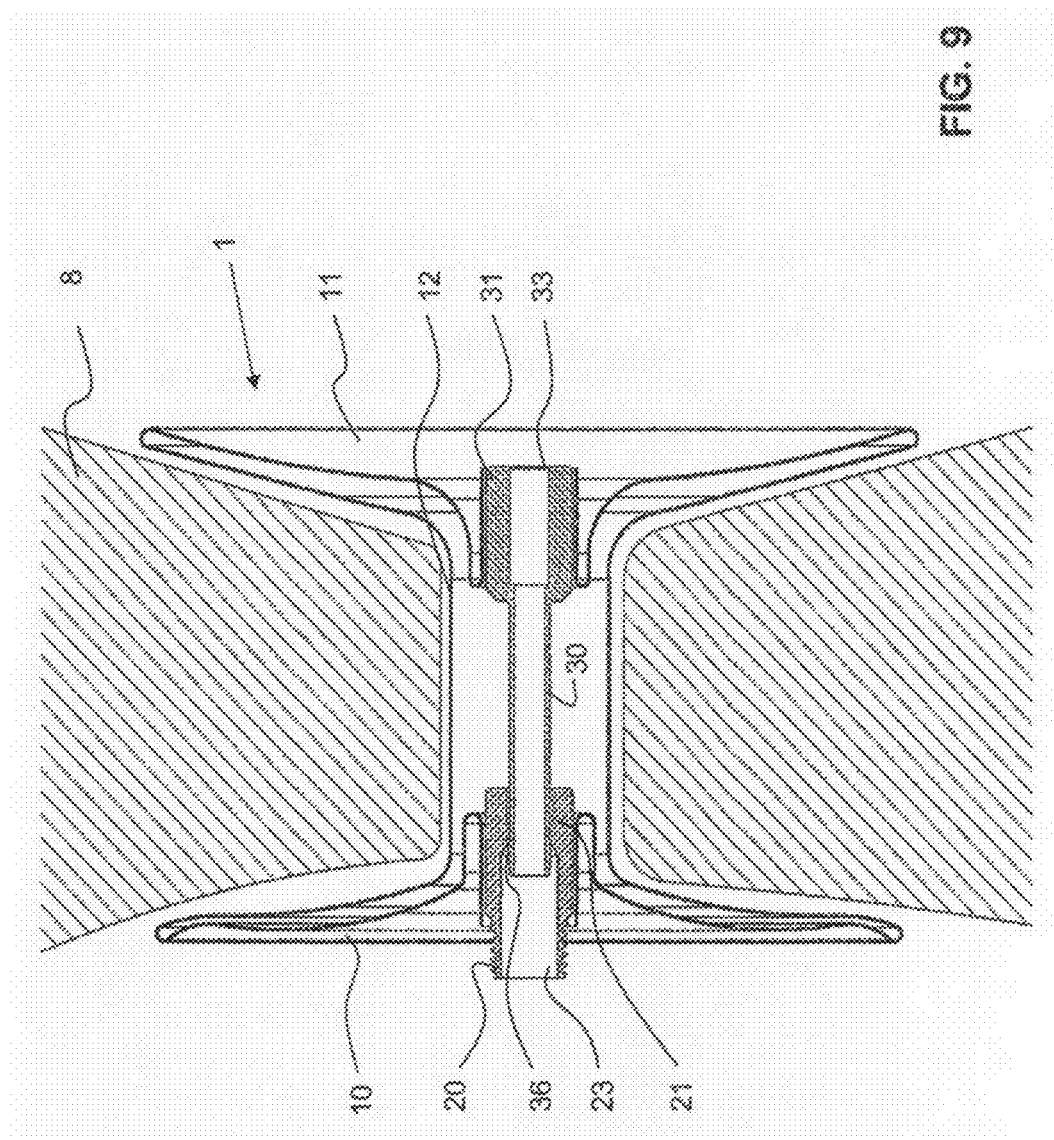

OCCLUDING DEVICE

FIELD OF THE INVENTION

This invention relates to an occluding device for closing a body passage such as a septal defect and a method for delivering an occluding device.

BACKGROUND OF THE INVENTION

Abnormal openings, holes or shunts can occur between the chambers of the heart or the great vessels, causing shunting of blood through the opening or the passage. Such abnormal openings can for example occur as ventricular septal defects, atrial septal defects and patent ductus arteriosus. In order to avoid morbidity and mortality associated with open-heart surgery a variety of transcatheter closure techniques have been attempted. In these techniques an occluding device is delivered through a catheter. Once the occluding device is positioned adjacent the defect, it must be attached to the rest of the septum in a manner which permits it to effectively block the passage of blood through the defect.

U.S. Pat. No. 4,836,204 describes an occluder consisting of two inflatable balloons made of latex or rubber. The two balloons are spaced from each other by a shaft of a catheter. The balloons are inflated and they close the passage in their inflated shape. This occluder needs quite a lot of space and can therefore not be used for closing small openings.

WO 97/41779 discloses an occluding device comprising a fluid tight inflatable double chamber balloon. A connection part between the two chambers is arranged to form guidance for the two chambers around a peripheral edge of the passage to be closed. Both chambers can be dilated radially by a number of stiffening means. These stiffening means are in a first embodiment metallic coils springs arranged in the chambers and in a second embodiment metallic threads. A locking mechanism comprising two snap together members arranged at each end of the balloon is provided for fixing the balloon in its dilated and evacuated position or for locking the threads in a twisted spring-like position. Metallic parts can however have a negative impact in view of cardiac arrhythmias.

FR 2 714 284 describes an occluder with a double chamber balloon, the balloon being made of a material with shape memory properties. The distal end of the balloon is closed and the proximal end comprises a valve. The balloon is inflated and placed at the location of the defect. It is then evacuated. The catheter is left in place for a certain period of time to make sure that the balloon remains at the chosen location.

The occluders according to the state of the art have the disadvantage that they are complicated in their construction and therefore also quite complicated to handle. In particular, when they are at the location of the defect, their final location and their shape can hardly be manipulated or affected.

U.S. Pat. No. 6,692,494 discloses a device to produce and maintain collateral openings or channels through an airway wall so that expired air is able to pass directly out of the lung tissue to facilitate both the exchange of oxygen into the blood and/or to decompress hyper-inflated lungs. The device can be delivered using an hour glass shaped balloon catheter. This balloon is removed after the device is delivered.

SUMMARY OF THE INVENTION

It is an object of the invention to provide a quite simple but well-working occluding device for closing a passage in a human or animal body.

This object is achieved with an occluding device for closing a body passage, the device comprising an occluding body, a first position control element and a second position control element. The occluding body is a balloon made of a flexible and fluid tight material without shape memory property. The balloon comprises a distal chamber and a proximal chamber and a connecting channel connecting these two chambers. The balloon is compressible into a first longitudinal shape. A proximal end of the balloon is attached to the first position control element and the distal end of the balloon is attached to the second position control element. The first position control element and the second position control element are two matching parts of a fluid tight closure of the balloon. The occluding body is adapted to be brought into a second inflated shape by introduction of a fluid and into a third radially extended but longitudinally compressed shape by evacuating this fluid and by bringing the two position control elements into a snapped together position. No additional stiffening means for stiffening the balloon in its third radially extended but longitudinally compressed shape are arranged within the balloon.

This occluding device can be adapted in its shape at the location of the defect and it can be rearranged even in its expanded state.

This occluder needs hardly any or no metal components or complicated materials. Since the occluder comprises no wires, the risk of fracture of the occluder structure or/and the risk of perforation of the patient's tissue is minimized. Since the occluder comprises no wires, the occluder is furthermore quite soft and non-conducting. This helps to prevent AV block (atrioventricular block).

The inventive occluder is especially well suited to be used in places with little space or places with a high damage risk. Occluders with wires need more space to deploy than they need in the end to occlude the defect. The wires can get entangled with neighbouring tissue and damage it. The inventive occluder expands softly and pushes the environment away without damaging it. Especially the risk to damage any heart valve is minimized.

In a preferred embodiment of the invention the occluder is at least partly made of biodegradable material.

Since the material of the occluding body has no shape memory properties the position control elements define its shape, wherein the two position control elements can be activated separately so that the balloon chambers can be mechanically changed in their shape separately from each other. Like this the two balloon chambers can be separately brought into their expanded but longitudinally compressed third shape, wherein the user can choose if he wants to bring the distal chamber first into this state or the proximal chamber or both chambers at the same time. This gives the user more possibilities to place the occluder at an optimal location within the defect and to rearrange it in the defect. The same size and shape of occluder can be used for different kinds and sizes of defects. Furthermore the balloon size and shape can be chosen from a variety of sizes and shapes and can be optimized for the kind of defect to be closed. Preferably the balloon is preshaped, for example his not inflated form already corresponds to an hour glass and this form is mainly just enlarged when inflated.

It is another object of the invention to provide an improved method to deliver an occlusive device to a passage to be closed of a human or animal body.

This inventive method for occluding a body passage with an occluding device, comprising the steps of
providing an occlusive device, the occlusive device comprising an occluding body in the shape of a double chamber balloon, a first position control element and a second position control element, wherein the occluding body comprises a proximal end connected to the first position control element and a distal end connected to the second position control element, providing a delivery system for delivering the occlusive device to the passage to be closed, the delivery system comprising a proximal control catheter with a distal end and a distal control catheter with a distal end, the proximal control catheter being penetrated by the distal control catheter and the two rods being moveably in longitudinal direction independently from each other, and the catheter delivery system comprising a pressure device, connecting the first position control element to the distal end of the proximal control catheter and the second position control element to the distal end of the distal control catheter, changing the distance between the distal ends of the distal control catheter and the proximal control catheter for compressing the occluding body into a longitudinal first shape, delivering the occlusive device to the passage to be closed and placing the device such that one chamber of the balloon is located on one side of a passage wall and another chamber of the balloon is located on another side of the passage wall, inflating the occluding body with the pressure device into a inflated second shape without using any additional stiffening means, checking the position of the occlusive device and if appropriate rearranging the occlusive device by pushing and pulling the first and second position control elements with the catheter and distal control catheter respectively, deflating the occluding body with the pressure device and reducing the distance of the distal ends of the proximal control catheter and distal control catheter thereby approaching the two position control elements to each other until they snap together to form a snap closure and removing the distal control catheter and the proximal control catheter from the now closed passage.

Since the occluder can be deflated to achieve adhesion to the human or animal tissue, and the proximal and distal chambers can be moved and compressed in longitudinal direction almost independently from each other, the occluder is very adaptive to different anatomical shapes. The deflated occluder cannot move any more, so that the catheter has not to be left in the patient after deployment of the occluder.

Further preferred embodiments of the invention are described in the dependent claims.

BRIEF DESCRIPTION OF THE DRAWINGS

The present invention will be more clearly understood with reference to the following detailed description of a preferred embodiment, taken in conjunction with the accompanying drawings, in which

FIG. 7 shows a side view of the occluder partly being in a third enlarged but longitudinally compressed state;

FIG. 8 shows an alternative to FIG. 7 and

FIG. 9 shows a longitudinal section of the occluder according to FIG. 8.

DESCRIPTION OF A PREFERRED EMBODIMENT

Figure 1:
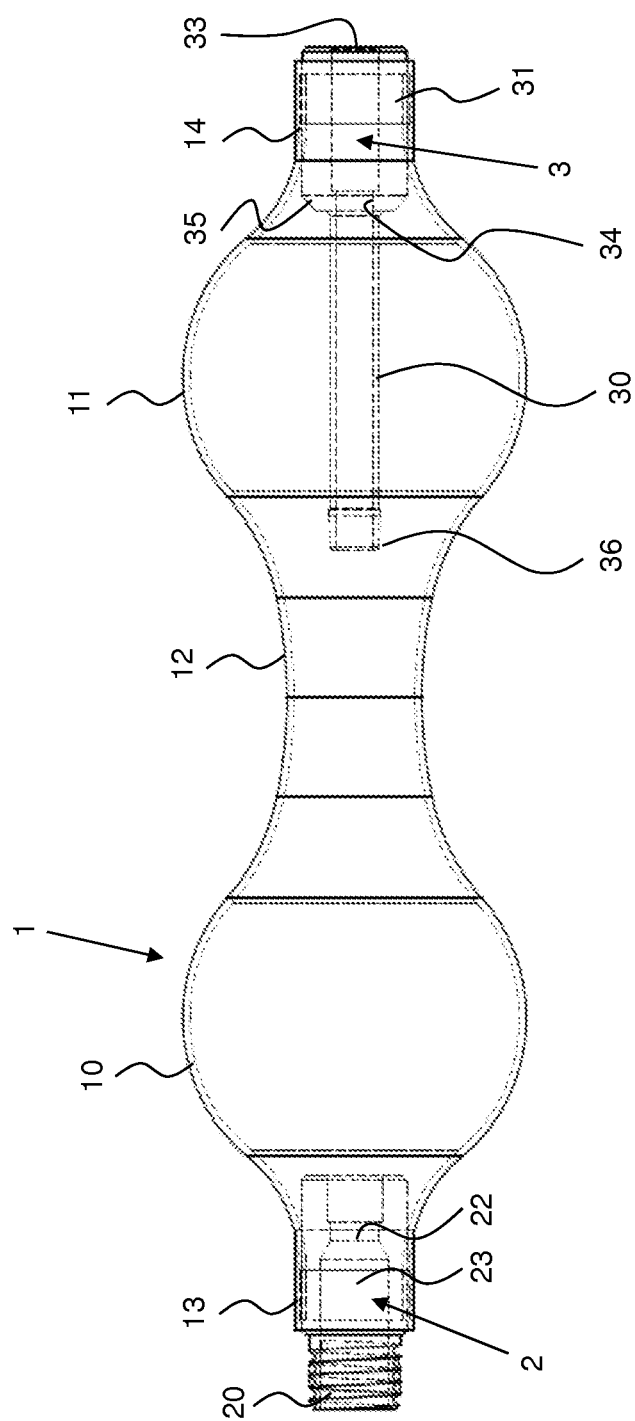
FIG. 1 shows side view of an occluding device according to the invention.

FIG. 1 shows an occluder for closing a body passage according to the invention in its original shape before use. The occluder comprises an occluding body 1, a first position control element 2 and a second position control element 3. Preferably the position control elements 2, 3 are a distal and a proximal end piece of the occluder.

The occluding body 1 is a shell or balloon made of a flexible and fluid tight material without shape memory property. Preferably the balloon is made of PET (Polyethylenterephtalat), nylon or another elastic or inelastic, but flexible material. The balloon comprises a proximal chamber 10, a distal chamber 11 and a connecting channel 12 connecting these two chambers. The two chambers 10, 11 and the connecting channel 12 form one single cavity. Preferably the balloon is single-piece. The lines in the figures are only considered to show the shape of the balloon in a better way but they are no real lines, especially no dividing lines or seams.

In its original state before use, the proximal chamber 10 can have the same size and shape as the distal chamber 11. However the two chambers 10, 11 can have different sizes and shapes as well. The size and shape depend on the kind of defect the occluder is supposed to close.

The connecting channel 12 has a smaller diameter than the two chambers 10, 11. Typical sizes of the diameter of the chambers 10, 11 are 5 to 50 mm, typically 15 mm and of the diameter of the connecting chamber 12 2 to 30 mm, typically 6 mm. Typical sizes of the length of the balloon are 30 to 150 mm. The thickness of the balloon wall is preferably overall the same and lies in the range of 0.01 to 0.15 mm.

A proximal end of the balloon forms a first attachment region 13 and a distal end of the balloon forms a second attachment region 14. Both regions 13, 14 are fixed, preferably welded, glued or pressed to a main body 21, 31, of the first and second position control element 2, 3 respectively. These connections are preferably fluid tight, in particular airtight. The balloon can additionally to welding and gluing or instead of these fixations also be fixed with rings which surround first and second position control element 2, 3 and which press the balloon material against the outer surface of these elements. These rings are not shown in the figures.

The position control elements 2, 3 are preferably made of plastic, for example PEEK (polyetheretherketone). Their main bodies 21, 31 are preferably of a tubular shape with an outer surface for attachment to the attachment regions 13, 14 of the balloon 1.

The proximal first position control element 2 has a clearance hole or a passage 23, which is big enough to be penetrated by a distal control catheter 60 mentioned underneath. Its main body 21 ends at its proximal end in an external thread 20. In the distal end region, it has an internal tapering 22, which narrows the internal passage 23.

The distal second position control element 3 comprises a hollow shaft 30, which extends into the balloon 1. The shaft 30 is preferably longer than its main body 31 and also as the main body 21 of the first position control element 2. The proximal end of the shaft 30 is formed as resilient catches 36 comprising noses 32, which can be seen in FIG. 6. Within the shaft 30 and/or in the connecting region between shaft 30 and main body 31 the position control element 3 comprises an internal thread 34. Since the shaft 30 has a smaller diameter than the main body 31, this region comprises a circumferential shoulder 35. The thread 34 can be one piece with the main body 31. Preferably the thread 34 is part of a metal tube which is pressed into the control element 3. This can be the only metal piece of the occluder. However in addition or instead of this metal part other parts can be made of metal as well.

This occluding device is preferably delivered over a catheter or a guide wire placed through the defect to be closed. Other ways of delivery are possible as well.

Figure 2:
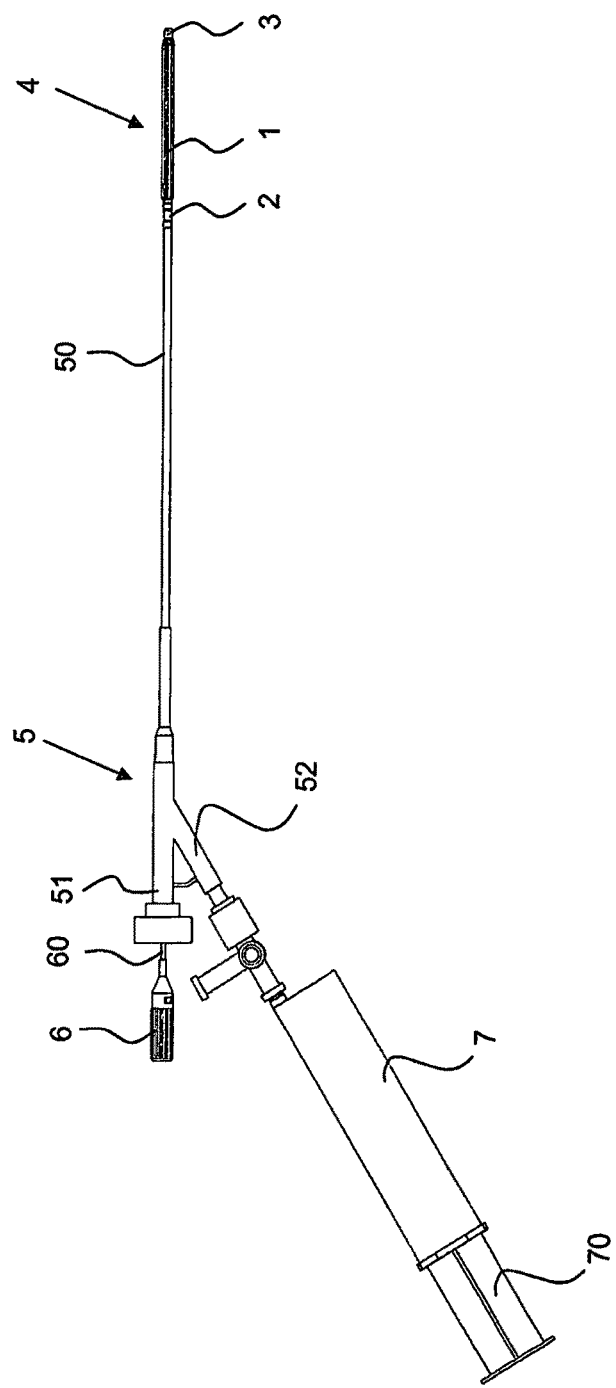
FIG. 2 shows a side view of a catheter carrying the occluder according to FIG. 1 in a first compressed state.

FIG. 2 shows the first way of delivery using a catheter delivery system. The occluding device bears here the reference number 4.

The catheter delivery system comprises a y-connector 5 with a proximal control catheter 50 and two arms 51, 52. The proximal control catheter 50 comprises at its distal end an internal thread 54, which can engage the external thread 20 of the first position control element 2 and which therefore connects the catheter 50 with this first element 2. Like this the occluder 4 is fixed with his proximal end to the catheter delivery system. A distal control catheter 60, which extends through the first arm 51, penetrates the proximal control catheter 50 and ends on its proximal end in a handle 60 and on its distal end in an external thread 63 which can be connected to the internal thread 34 of the second position control element 3. The distal tip with the thread 63 can be a separate insert 61, which is connected with the distal control catheter 60. For example, it can be glued or screwed. In a preferred embodiment, the distal tip is an integral part of the distal control catheter 60.

The distal end carrying the internal thread 54 of the proximal control catheter 50 as well can be a separate insert 53, which is can for example be connected to the proximal control catheter 50 by an adhesive or with threads. This can be seen in FIG. 6. However it can also be an integral part of the proximal control catheter 50.

The distal end of the occluder 4 is fixed to the catheter delivery system as well, but independently from the fixation of its proximal end.

Instead of threads other well known kinds of connections for connecting the catheters to the main bodies can be used as well.

Figure 3:
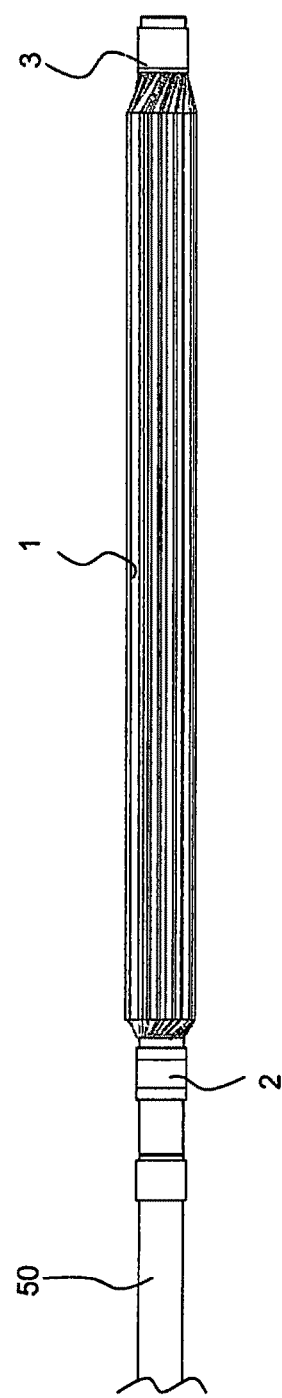
FIG. 3 shows a detail of FIG. 2 in an enlarged depiction.

By controlling the distance between the two distal ends of the distal control catheter 60 and the proximal control catheter 50, the occluder 4 is compressed in an elongate first shape, as can be seen in FIG. 2 and in more detail in FIG. 3. In this state, the occluder 4 can be deflated as well, preferably by use of the syringe 7 mentioned below.

The catheter delivery system comprises an evacuation device, here a syringe 7 as well. Instead of a syringe, a small manual or electronic pressure pump can be used as well. This syringe 7 is connected to the second arm 52. By use of the piston 70 of the syringe 7, the balloon 1 of the occluder 4 can be inflated and deflated, the latter situation being shown in FIGS. 2 and 3. The outer diameter of the occluder 4 is in this state small enough to be delivered through a body channel, such as a vein or another vessel. Typical sizes for this minimized outer diameter are 1 to 3 mm.

Figure 4:
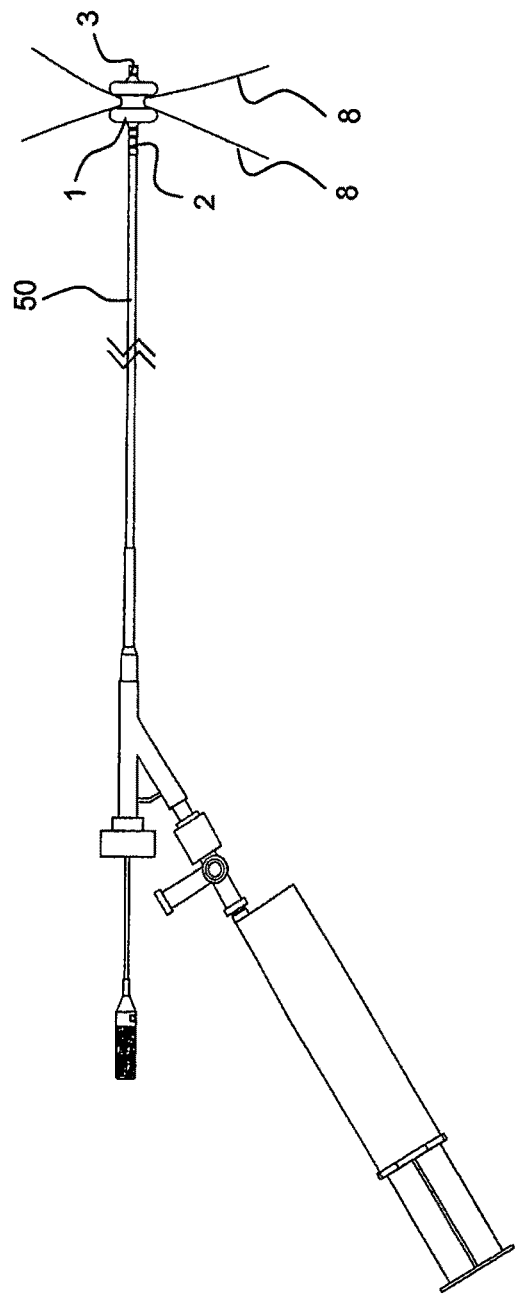
FIG. 4 shows a side view of the catheter according to FIG. 2 with the occluder in a second inflated state within an anatomical structure.
Figure 5:
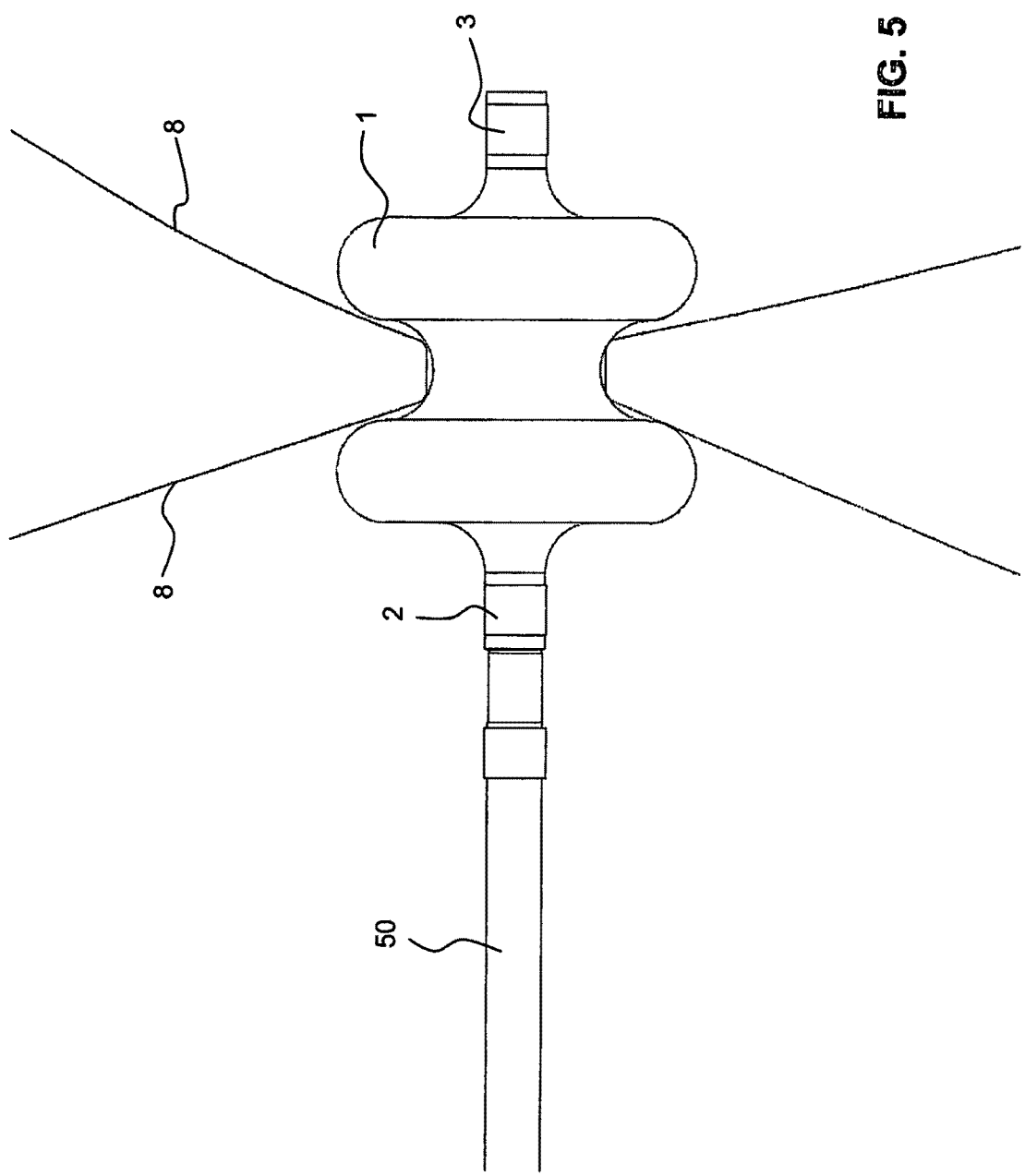
FIG. 5 shows a detail of FIG. 4 in an enlarged depiction within an anatomical structure.

When the occluder 4 has reached the location of the defect and the occluder is placed at both sides of the passage wall 8, the balloon 1 is inflated with a contrast-agent to check its position. The occluder is now in its second inflated state. This situation is shown in FIG. 4 and in more detail in FIG. 5. Instead of a contrast-agent, another fluid can be used as well.

The proximal chamber 10 is arranged on the proximal side of the passage wall 8, the distal chamber 11 on the distal side. The connecting channel 12 forms a guidance for the two chambers 10, 11 around a peripheral edge of the passage wall 8 and it centers the occluder in the defect.

In the correct position, no residual shunt should be seen. By using the two position control elements 1, 2, which are independently connected to the distal control catheter 60 and the proximal control catheter 50 respectively, a push and pull maneuver can be performed to rearrange the occluder and to ensure the correct sitting of the occluder in the defect. This means, the first control element 2 can be pushed or pulled and at the same time or afterwards the second element 3 can be pulled and pushed in the other direction. The rearrangement preferably comprises centralization of the occluder in the defect and adapting the shape of the occluder in its third state to the anatomical structure.

Figure 6:
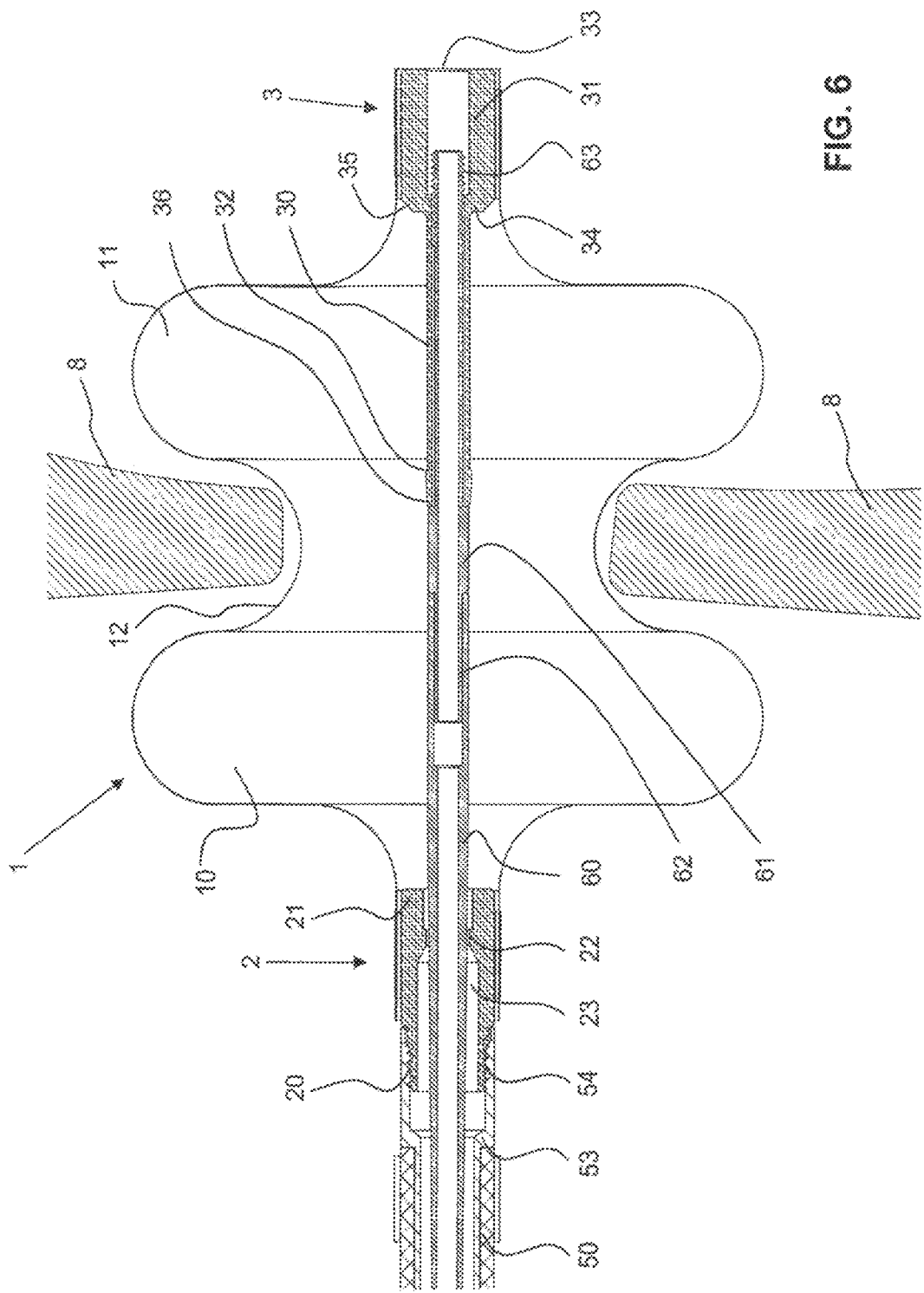
FIG. 6 shows a longitudinal section of the detail according to FIG. 5.

FIG. 6 shows this situation as well, wherein the engagements of the distal control catheter 60 and the proximal control catheter 50 with the two separate position control elements 2, 3 can be seen. The distal control catheter 60 can but does not have to be well guided in these last centimeters, since it is guided by the tapering 22 within the first position control element 2 and it is connected to the second position control element 3 at a short distance afterwards due to the shaft 30 extending within the balloon 1.

After the occluder 4 is in the correct position, the two control elements 2, 3 are approached to each other while the contrast-agent is removed through the catheter delivery system. When approaching them to each other, the user can choose if he wants to first compress the distal balloon chamber 11 or the proximal balloon chamber 10. In FIG. 7, the distal chamber 11 is first compressed, in FIG. 8, it is the proximal chamber 10. It is possible to compress them simultaneously as well. Furthermore, the suction by use of the syringe 7 can be utilized to adapt the shape of the occluder to the patient's anatomy. As can be seen in FIGS. 7 and 8 the same occluder size can be used for different sizes of defects, especially for passage walls 8 with different thicknesses. In FIG. 7 the wall is quite thin, in FIG. 8 it is quite thick. The two chambers 10, 11 and the connecting channel 12 adapt their shape to the respective anatomy.

FIG. 9 shows the third and final state where the occluder is radially extended but longitudinally compressed. By retracting the distal control catheter 60 the shaft 30 of the second element 3 has snapped into the main body 21 of the first element 2 and is hold back by its noses 32 of the resilient catches 36, which engage with the tapering 22. The two position control elements 2, 3 form the two matching parts of a snap closure. This fixation ensures stability of the position and shape of the occluder within the defect. Other known kind of closures can be used instead of a snap closure. The closure has to close the interior of the balloon so that it is fluid tight. However the closure itself can still form an open passage through the occluder, as can be seen in FIG. 9. There does still exist an open channel through the main bodies 21, 31, wherein the interior of balloon is closed relative to the environment. The closure, especially the snap closure, can preferably be opened again within the location. Therefore, the balloon can again be inflated and rearranged, as long as the balloon material is not grown together with the patient's tissue.

The snap closure is preferably fluid-tight, so that the inner cavity of the occluder is now sealed against the environment. The removal of the contrast-agent has this cavity left with an underpressure or at least with no overpressure compared with the environment.

In this embodiment, the shaft 30 was part of the second element 3. However, it can also be part of the first, proximal element 2. Furthermore, other snap elements than this fixably holdable shaft can be used as well.

As can be seen no additional stiffening means are needed within the occluder to obtain its different shapes. Like this the amount of metal forming part of the occluder can be minimized or brought to zero.

This occluder can be used for different kinds of defects, such as ventricular septal defects, atrial septal defects and patent ductus arteriosus. It is especially well suited to be used for VSD (ventricle septum defect).

The inventive occluder allows rearrangement of the balloon within the defect and it enables to adapt the shape of the balloon to the patient's anatomy.

LIST OF REFERENCE NUMBERS 1 occluding body
10 proximal chamber
11 distal chamber
12 connecting channel
13 first attachment region
14 second attachment region
2 first position control element
20 external thread
21 main body
22 tapering
23 passage
3 second position control element
30 shaft
31 main body
32 nose
33 closed wall
34 internal thread
35 shoulder
36 resilient catches
4 occluder
5 y-connector
50 proximal control catheter
51 first arm
52 second arm
53 insert
54 internal thread
6 handle
60 distal control catheter
61 insert
62 press fit
63 external thread
7 syringe
70 piston
8 passage wall

The invention claimed is:

1. An occluding device for closing a body passage, the occluding device comprising:
an occluding body,
a first position control element, and
a second position control element,
wherein the occluding body is a balloon made of a flexible and fluid tight material without a shape memory property, the balloon comprising a distal chamber, a proximal chamber, and a connecting channel connecting the two chambers,
a proximal end of the occluding body being fluid-tightly attached to the first position control element, and
a distal end of the occluding body being fluid-tightly attached to the second position control element,
the first position control element and the second position control element being two mating parts of a fluid tight closure of the balloon closing an interior of the balloon so that the interior is fluid tight,
the occluding body being compressible into a first longitudinal shape, the occluding body being adapted to be brought into a second inflated shape by introduction of a fluid and into a third radially extended but longitudinally compressed shape by evacuating the fluid and by bringing the two position control elements into a snapped together position,
wherein no additional stiffening means are present in the occluding device to obtain the third radially extended but longitudinally compressed shape, and wherein no additional stiffening means for stiffening the balloon in its third radially extended but longitudinally compressed shape are arranged within the balloon, and wherein the two position control elements form an open passage through the balloon in the third shape.

2. The device according to claim 1, wherein the occluding body is a single piece balloon.

3. The device according to claim 1, wherein the closure is a snap closure.

4. The device according to claim 1, wherein the first position control element comprises an external thread and a passage.

5. The device according to claim 1, wherein the second position control element comprises an internal thread.

6. The device according to claim 1, wherein the closure can be opened again.

7. The device according to claim 1, wherein the connecting channel has a smaller diameter than the proximal and the distal chamber.

8. The device according to claim 1, wherein the occluding body is made of PET (Polyethylenterephtalate) or nylon.

9. The device according to claim 1, wherein the first and the second position control elements are made of plastic.

10. The device according to claim 1, wherein the device is non-metallic.

11. The device according to claim 1, wherein the first and the second position control element each comprise a main tubular body with an outer surface and wherein the occluding body comprises a proximal and a distal tubular attachment region, wherein the proximal and distal tubular attachment regions are attached to the outer surfaces of the main bodies of the position control elements.

12. The device according to claim 11, wherein the attachment regions are welded, glued or pressed to the main bodies.

13. The device according to claim 1, wherein the first or the second position control element comprises a shaft and the other of these two position control elements comprises a space, in which the shaft is fixably holdable.

14. The device according to claim 13, wherein the shaft comprises resilient catches which engage into the other position control element.

15. The device according to claim 13, wherein the shaft is part of the second position control element.

16. The device according to claim 13, wherein the shaft extends into the occluding body.

17. A method for occluding a body passage with an occluding device, comprising the steps of:
providing an occlusive device, the occlusive device comprising an occluding body in the shape of a double chamber balloon, a first position control element and a second position control element, wherein the occluding body comprises a proximal end fluid-tightly connected to the first position control element and a distal end fluid-tightly connected to the second position control element, providing a delivery system for delivering the occlusive device to the passage, the delivery system comprising a proximal control catheter with a distal end and a distal control catheter with a distal end, the proximal control catheter being penetrated by the distal control catheter and the two catheters being moveable in a longitudinal direction independently from each other, and the catheter delivery system comprising a pressure device, connecting the first position control element to the distal end of the proximal control catheter and the second position control element to the distal end of the distal control catheter, changing the distance between the distal ends of the distal control catheter and the proximal control catheter for compressing the occluding body into a longitudinal first shape, delivering the occlusive device to the passage and placing the device such that one chamber of the balloon is located on one side of a passage wall and another chamber of the balloon is located on another side of the passage wall, inflating the occluding body with the pressure device into an inflated second shape and holding the occluding body in the inflated second shape without using any additional stiffening means, checking the position of the occlusive device and if appropriate rearranging the occlusive device by pushing and pulling the first and second position control elements with the catheter and distal control catheter respectively, deflating the occluding body with the pressure device and reducing the distance of the distal ends of the proximal control catheter and distal control catheter thereby approaching the two position control elements to each other until they snap together to form a fluid tight closure for the balloon closing an interior of the balloon so that the interior is fluid tight, removing the distal control catheter and the proximal control catheter from the occluded passage; and leaving the occluding body deflated in the body passage.

18. An occluding device for closing a body passage, the occluding device comprising:
an occluding body,
a first position control element, and
a second position control element,
wherein the occluding body is a single piece balloon made of a flexible and fluid tight material without a shape memory property, the balloon comprises a distal chamber, a proximal chamber, and a connecting channel connecting the two chambers,
a proximal end of the occluding body being fluid-tightly attached to the first position control element, and
a distal end of the occluding body being fluid-tightly attached to the second position control element,
the first position control element and the second position control element being two mating parts of a fluid tight closure of the balloon closing an interior of the balloon so that the interior is fluid tight,
the occluding body being compressible into a first longitudinal shape,
the occluding body being adapted to be brought into a second inflated shape by introduction of a fluid and into a third radially extended but longitudinally compressed shape by evacuating the fluid and by bringing the two position control elements into a snapped together position,
wherein no additional stiffening means for stiffening the balloon in its third radially extended but longitudinally compressed shape are arranged within the balloon, and wherein the two position control elements form an open passage through the balloon in the third shape.

19. An occluding device for closing a body passage, the occluding device comprising:
an occluding body,
a first position control element, and
a second position control element,
wherein the occluding body is a balloon made of a flexible and fluid tight material without a shape memory property, the balloon comprising a distal chamber, a proximal chamber, and a connecting channel connecting the two chambers, wherein the distal chamber, the proximal chamber, and the connecting channel form one single cavity,
a proximal end of the occluding body being fluid-tightly attached to the first position control element, and
a distal end of the occluding body being fluid-tightly attached to the second position control element,
the first position control element and the second position control element being two mating parts of a fluid tight closure of the balloon closing an interior of the balloon so that the interior is fluid-tight,
the occluding body being compressible into a first longitudinal shape,
the occluding body being adapted to be brought into a second inflated shape by introduction of a fluid and into a third radially extended but longitudinally compressed shape by evacuating this fluid and by bringing the two position control elements into a snapped together position,
wherein no additional stiffening means for stiffening the balloon in its third radially extended but longitudinally compressed shape are arranged within the balloon, and wherein the position control elements form an open passage through the balloon in the third shape.

* * * * *